United States Patent [19]
Yokota et al.

[11] 3,950,409
[45] Apr. 13, 1976

[54] PROCESS FOR CONTINUOUS PREPARATION OF TEREPHTHALIC ACID

[75] Inventors: Yoshiro Yokota, Ohtake; Toshihiko Ueda; Osamu Nakano, both of Iwakuni; Sigeru Hirokane, Waki; Yoshiro Hisatomi, Iwakuni, all of Japan

[73] Assignee: Mitsui Petrochemical Industries, Ltd., Tokyo, Japan

[22] Filed: Mar. 25, 1974

[21] Appl. No.: 454,414

[30] Foreign Application Priority Data
Apr. 5, 1973 Japan................................ 48-38277

[52] U.S. Cl............................................. 260/524 R
[51] Int. Cl.²........................................ C07C 51/33
[58] Field of Search ................................ 260/524 R

[56] References Cited
UNITED STATES PATENTS
2,964,559  12/1960  Burney et al.................... 260/524 R

*Primary Examiner*—Anton H. Sutto
*Attorney, Agent, or Firm*—Sherman & Shalloway

[57] ABSTRACT

An improved process for continuously preparing terephthalic acid by a catalytic liquid-phase oxidation which comprises recycling a part of the mother liquor of the oxidation product to the catalytic liquid-phase oxidation zone either as such or after concentration, concentrating the remainder of the mother liquor, until the amount of acetic acid in the resulting bottoms becomes not more than 5% by weight based on the weight of the residual bottoms and the amount of benzoic acid bottoms becomes not less than 15% by weight based on the weight based on the weight of the residual bottoms, contacting the bottoms in the hot and molten state with 2 to 5 times their weight of water, and rapidly cooling the bottom to a temperature of not more than 50°C., separating an aqueous solution containing the catalyst from the resulting granular solid mixture and recycling the aqueous solution to the catalytic liquid-phase oxidation zone.

5 Claims, No Drawings

PROCESS FOR CONTINUOUS PREPARATION OF TEREPHTHALIC ACID

This invention relates to a process for continuously preparing terephthalic acid by the catalytic liquid-phase oxidation of para-xylene wherein a catalyst-containing aqueous solution is recovered by an easy operation from the mother liquor, with good efficiency of extracting the catalyst and at a high rate of removal of undesirable organic by-products, and is recycled to the oxidation reaction, thereby to prepare terephthalic acid with commercial advantage.

More specifically, this invention relates to a process for continuously preparing terephthalic acid which comprises oxidizing para-xylene with molecular oxygen in the liquid phase in acetic acid in the presence of a heavy metal oxidation catalyst, separating and collecting terephthalic acid from the resulting oxidation reaction mixture, recycling a part of the mother liquor to the catalytic liquid-phase oxidation zone either as such or after concentration, concentrating the remainder of the mother liquor, extracting the residual bottoms containing the heavy metal oxidation catalyst and the organic by-products with water, and recycling the resulting catalyst-containing aqueous solution to the above catalytic liquid-phase oxidation zone; wherein 1. the concentration is performed until the amount of acetic acid in the bottoms becomes not more than 5 % by weight based on the weight of the residual bottoms and the amount of benzoic acid in the bottoms becomes not less than 15 % by weight based on the weight of the residual bottoms,
2. the bottoms are contacted in the hot and molten state with 2 to 5 times their weight of water, and rapidly cooled to a temperature of not more than 50°C., and
3. an aqueous solution containing the catalyst is separated from the resulting granular solid mixture consisting of organic by-products and catalyst-containing aqueous solution, and the aqueous solution so separated is recycled to the catalytic liquid-phase oxidation zone (if desired, it can be recycled after being concentrated).

It is well known to prepare terephthalic acid by liquid-phase oxidation of para-xylene with molecular oxygen (the term meant to include a gas which contains molecular oxygen) in acetic acid in the presence of a catalyst comprising a compound of a heavy metal such as cobalt or manganese and a bromine-donating substance, or in the further presence of an activator such as a ketone or aldehyde. In this process, the mother liquor resulting from the separation of the resulting terephthalic acid from the reaction mixture consists of the acetic acid used as solvent, the heavy metal compound and bromine-donating substance used as catalyst, and occasionally the ketone or aldehyde as activator, and organic by-products composed of oxidation intermediates or oxidation by-products. In order to utilize such an expensive catalyst effectively, it would be appropriate to recycle all of the mother liquor to the oxidation system. However, since the mother liquor contains by-products which restrict or inhibit the oxidation of para-xylene, it is virtually impossible to recycle all the mother liquor to the oxidation system because of the possible contamination of the catalyst and the terephthalic acid. In the continuous manufacture of terephthalic acid in which the mother liquor is recycled to the catalytic liquid-phase oxidation reaction system, the organic impurities must be removed from the mother liquor to an extent such that their amounts do not exceed the allowable limits.

Methods for treating the mother liquor with water are disclosed, for example, in U.S. Pat. No. 2,964,559 (issued on Dec. 13, 1960), and Japanese Laid-Open Publication No. 42735/72 (laid open on Dec. 16, 1972).

In the U.S. Pat., the heavy metal oxidation catalyst is extracted from a distillation bottoms fraction which contains heavy metal oxidation catalyst and tar-like oxidation inhibiting by-products at a temperature between about 50° and 150°C. with water in an amount between about 3 to about 50 volumes per volume of distillation bottoms. The U.S. Patent discloses that the distillation bottoms may be extracted while the bottoms are hot molten liquids, or can be extracted in the form of pulverized or flaked solids. In the Examples, volatile aromatic acids such as benzoic acid or phthalic anhydride or aliphatic monocarboxylic acids as solvents which are likely to be dissolved in the aqueous phase upon contact with water are completely distilled off by repeated distillation of the mother liquor to obtain distillation bottoms in the water insoluble state. The bottoms are pulverized and the heavy metal oxidation catalyst is extracted from the bottoms. This extraction process has the advantage that undesirable organic by-products are unlikely to be extracted into the aqueous phase, but on the other hand, suffers from the disadvantages that the mother liquor should be repeatedly distilled until the distillation bottoms become water-insoluble, there is a great thermal loss, and a step of pulverizing the bottoms is required. In order to extract the heavy metal oxidation catalyst with good efficiency from such a solid, a considerably high extracting temperature and a long period of time are required, and the extracting effect is low.

The method disclosed in the Japanese Laid-Open Publication comprises separating and collecting terephthalic acid from the reaction mixture, then distilling the mother liquor until its acetic acid content becomes 10 to 50 % by weight, adding to the resulting concentrated acetic acid solution 1 to 10 times the amount of water at 10° to 40°C., and thus precipitating the organic by-products utilizing the difference in solubility in water at low temperatures between the catalyst and the organic by-products, and extracting the catalyst into the aqueous phase. According to this method, the heavy metal oxidation catalyst can be well extracted, but since acetic acid is present in a considerably great amount, considerable amounts of the organic by-products remain dissolved in the acetic acid, which makes it impossible to precipitate all the organic by-products containing oxidation inhibiting by-products. Especially when the amounts of water-soluble organic by-products increase, the amounts of the by-products dissolved in the aqueous phase increase. Furthermore, in such a case, an aqueous emulsion tends to be formed, and the separation of the organic by-products becomes more difficult. As a result, the oxidation inhibiting by-products accumulate in the catalytic liquid-phase oxidation system. In order to avoid this difficulty, it is necessary to perform a disadvantageous pre-treatment whereby the water-soluble organic by-products are removed from the acetic acid solution obtained by concentrating the mother liquor by distillation or evaporation, or a disadvantageous post-treatment whereby a part of the resulting catalyst-containing aqueous solution is recycled so as to prevent the undesirable by-products dissolved in the aqueous solution from accumulating in the oxidation system in substantial amounts.

We have now found that the above disadvantages can be overcome in accordance with this invention by distilling or evaporating the mother liquor resulting from the separation and collection of terephthalic acid thereby to concentrate it, adjusting the amounts of acetic acid and benzoic acid in the residual bottoms to specific ranges, and contacting the residual bottoms in the hot and molten state containing the adjusted amounts of the acetic acid and benzoic acid with a specific amount of water, and rapidly cooling the bottoms to a temperature of not more than 50°C. It has also been found that by contacting the above residual bottoms in the hot and molten state containing the adjusted amounts of acetic acid and benzoic acid with the specific amount of water and rapidly cooling the bottoms to a specific temperature, the heavy metal oxidation catalyst is extracted into the aqueous phase with a high degree of selectivity, and the organic by-products which contain oxidation inhibiting by-products are removed as solids with a high degree of selectivity. Furthermore, as will be shown by a number of comparative experiments to be given later, where a combination of the above requirements is not met, either one or both of the selective extraction of the heavy metal oxidation catalyst and the selective removal of the undesirable organic by-products cannot be achieved.

We have confirmed that only when the combination of the above requirements is met, organic by-products which may contain water-soluble and oxidation inhibiting by-products rapidly solidify, without occluding a substantial amount of the heavy metal oxidation catalyst, to a granular solid having a relatively hard surface and being very difficult to dissolve again in the aqueous phase.

Accordingly, it is an object of this invention to provide an improved method for continuously preparing terephthalic acid, with the elimination of the above defects of the prior art, wherein a part of the mother liquor resulting from the separation of terephthalic acid is recycled to the catalytic liquid-phase oxidation zone, and the catalyst-containing aqueous solution is recovered from the remainder of the mother liquor, and the recovered aqueous solution is recycled to the oxidation zone. If desired, it can be recycled after being concentrated.

Many other objects of this invention along with its advantages will become more apparent from the following description.

According to the process of this invention, para-xylene is oxidized in a customary manner with molecular oxygen such as air in the liquid phase in acetic acid in the presence of a heavy metal oxidation catalyst, and terephthalic acid is separated and collected from the resulting oxidation reaction mixture. A part of the remaining mother liquor is recycled to the oxidation zone in a customary manner either as such or after being concentrated. The remainder of the mother liquor is distilled or evaporated to concentrate it, and the remaining residual bottoms containing the heavy metal oxidation catalyst and organic by-products are extracted with water. The resulting catalyst-containing aqueous solution is recycled to the liquid-phase oxidation zone.

According to this invention, the remainder of the mother liquor is concentrated until the content of acetic acid in the residual bottoms is not more than 5 % by weight, preferably 2 % by weight, more preferably 1 % by weight, based on the weight of the residual bottoms, and the content of benzoic acid which may be formed by the oxidation reaction and also may be formed by the oxidation reaction of monoalkyl benzenes existing as an impurity of para-xylene is not less than 15 %, preferably 20 % by weight based on the weight of the residual bottoms. More preferably, the concentration is carried out until the content of isophthalic acid in the residual bottoms is not less than 3 % by weight based on the weight of the residual bottoms, and the content of para-toluic acid is not less than 3 % by weight based on the weight of the residual bottoms. If the amount of acetic acid in the residual bottoms exceeds the upper limit specified above, substantial amounts of the undesirable organic by-products dissolve and/or disperse in the resulting catalyst-containing aqueous solution, and it is impossible to obtain a catalyst-containing aqueous solution having selectively extracted the heavy metal oxidation catalyst therein.

If the concentration is performed excessively and benzoic acid too is evaporated to an extent that its amount becomes smaller than the lower limit of the above-specified amount, the molten residue solidifies too rapidly upon cooling to form a large mass. As a result, the extraction of the catalyst into the aqueous solution cannot be carried out with good efficiency.

The objects of this invention cannot be achieved merely by concentrating the residual bottoms to specific contents of acetic acid and benzoic acid [requirement (1)], but it is necessary that the residual bottoms are contacted with 2 to 5 times the weight of the bottoms of water while the bottoms are hot molten liquids, and to rapidly cool the bottoms to a temperature of not more than 50°C., preferably 20° to 50°C. [requirement (2)].

The requirement (2) is important in a combination with the requirement (1), and if either one of them is not met, the objects of this invention cannot be achieved. Although it is not clear why the combination of these requirements (1) and (2) is essential in the process of this invention, the results of Comparative Experiments to be given later show that the combination of the requirements (1) and (2) greatly contributes to the solidification of organic by-products, which may contain water-soluble or water-emulsifiable and oxidation inhibiting by-products, to particles having sizes and surface conditions suitable for extraction of the heavy metal oxidation catalyst into the aqueous phase.

The residual bottoms can be maintained in the hot and molten state in the process of this invention by heating the bottoms to a temperature above the melting point of benzoic acid. The contact between the hot and molten residual bottoms and water can be carried out by adding water to the bottoms with stirring. The temperature and amount of the water or the stirring conditions can be suitably adjusted in performing the desired rapid cooling. If necessary, other cooling means can be used conjointly. It is desirable that the rapid cooling should be carried out by adding the molten residual bottoms and water to an extracting tank while maintaining the temperature of the extracting tank at not more then 50°C. The temperature of the extracting tank is maintained at the desired temperature by a general method such as by using a cooler (e.g., a jacket), or by conducting the mixture to a cooler and circulating it after cooling.

When the temperature of the extracting tank does not reach below 50°C., the organic by-products become emulsions, and come into the catalyst-containing aqueous solution withot becoming solidified to a granular solid. It is therefore necessary to cool the residual bottoms to a temperature of not more than 50°C. However, if the bottoms are rapidly cooled excessivly to low temperatures, the solidified particles of organic by-products become a large mass to render the extraction of the catalyst insufficient although the organic by-products are prevented from being incorporated into the catalyst-containing aqueous solution. Therefore, it is preferred that the temperature be adjusted to 20° to 50°C. The solidification of the organic by-products is effected instantaneously but in order to increase the rate of extracting the catalyst, it is preferred to stir the mixture for 10 to 30 minutes at a temperature of not more than 50°C.

The amount of water to be used to cool the bottoms to not more than 50°C. is restricted, and it is necessary to use water in an amount 2 to 5 times the weight of the residual bottoms. If the amount of water is insufficient, the organic by-products tend to become a large mass, and the rate of extracting the catalyst does not increase. On the other hand, if the amount of water is excessive, an emulsion of the organic by-products is formed, and the organic by-products which may contain oxidation inhibiting by-products come into the catalyst-containing aqueous solution. It is necessary therefore to adjust the amount of water to the above specified range.

The catalyst-containing solution is then separated from the resulting mixture which is in the form of a granular solid consisting of it and the organic by-products, and recycled to the catalytic liquid-phase oxidation zone. The separation can be performed by any liquid-solid separating means, for example, centrifugal separation. The separated catalyst-containing aqueous solution can be recycled to the catalytic liquid phase oxidation zone partly or wholly. If desired, it can be recycled after being concentrated.

The following Examples and Comparative Examples illustrate the process of this invention more specifically.

EXAMPLE 1

An oxidation reactor was continuously charged with 100 Kg/hr of para-xylene, 900 Kg/hr of acetic acid, and a catalyst (3.4 Kg/hr of cobalt acetate, 3.4 Kg/hr of manganese acetate and 1.7 Kg/hr of sodium bromide), and air was introduced continuously at a rate of 400 m$^3$/hr (in normal state) at 180°C. and 10 Kg/cm$^2$-G to oxidize the para-xylene while removing water formed as by-product. After a residence time of 1 hour, the oxidation reaction product was withdrawn continuously from the oxidation reactor, and 148 Kg/hr of terephthalic acid was separated by centrifugal separation from the reaction product. 95 % by weight of the resulting mother liquor was directly circulated to the oxidation reactor, and the remainder of the mother liquor was evaporated to concentrate it, and 1.5 Kg/hr of molten residual bottoms (0.5 % by weight acetic acid, 32 % by weight benzoic acid, 19 % by weight isophthalic acid, 14 % by weight para-toluic acid, 2 % by weight of para-formylbenzoic acid, 5 % by weight terephthalic acid, 25.5 % by weight of other organic impurities, and 2 % by weight catalyst) were obtained.

The residual bottoms in the molten state were continuously fed into an extraction tank provided with a stirrer, and brought into contact with three times their weight of water at room temperature, followed by rapid cooling to 40°C. by passing water through a jacket, thereby to solidify the organic by-products in a solid granular form. At the same time, the granular solid is maintained at 40°C. for 20 minutes to extract the catalyst. The effluent from the extraction tank was centrifugally separated into granular solid organic by-products (1.65 Kg/hr) and a catalyst-containing aqueous solution (4.35 Kg/hr). The catalyst-containing aqueous solution was concentrated, and recycled to the oxidation reactor. The operation was continuously performed for 2,000 hours, but no trouble occurred.

The content of the organic by-products in the catalyst-containing aqueous solution was 0.5 % by weight, and the rate of extraction was 90.6 % by weight for cobalt, 91.8 % by weight for manganese, and 80.6 % by weight for bromine. The rate of removal of the granular organic by-products from the residual bottoms was 98 % by weight.

COMPARATIVE EXAMPLE 1

The procedure of Example 1 was repeated except that residual bottoms (10 % by weight acetic acid, 29 % by weight benzoic acid, 17 % by weight isophthalic acid, 12.7 % by weight para-toluic acid, 1.8 % by weight paraformylbenzoic acid, 4.5 % by weight terephthalic acid, 23.2 % by weight other impurities, and 1.8 % by weight catalyst) in the molten state obtained by concentrating the remainder of the mother liquor to a lesser extent were used. An emulsion was formed, and consequently, the content of the organic by-products in the catalyst-containing aqueous solution was as high as 5.7 % by weight, whereas the rate of removal of the organic by-products from the residual bottoms was as low as 74 % by weight. It was impossible to continue the operation for prolonged periods of time.

COMPARATIVE EXAMPLE 2

The procedure of Example 1 was repeated except that rapid cooling was not effected at the time of contacting the molten residual bottoms with water at room temperature, but steam was passed through the jacket to maintain the mixture at 60°C. for 20 minutes. An emulsion was formed, and consequently, the rate of removal of the organic by-products from the residual bottoms was as low as 77 % by weight, whereas the content of the organic by-products in the catalyst-containing aqueous solution was as high as 5 % by weight. It was impossible to continue the operation for prolonged periods of time.

COMPARATIVE EXAMPLES 3, 4 and 5

The procedure of Example 1 was repeated except that in contacting the molten residual bottoms with water, the amount of water was changed to 1 time (by weight), 6 times (by weight), and 10 times (by weight) based on the residual bottoms, and the temperature of the mixture was maintained at about 40°C. by passing cooling water or steam through the jacket. It was found that when the amount of water was 1 time, the organic by-products became a mass, and the rate of extracting cobalt was as low as 62.3 %. When the amount of water was 10 times, an emulsion was formed, and the rate of removal of the organic by-products was as low as 69 % by weight. In either case, it was impossible to continue the operation for prolonged periods of time.

EXAMPLES 2, 3 and 4 and COMPARATIVE EXAMPLES 6, 7 and 8

The procedure of Example 1 was repeated except that the amounts of acetic acid and benzoic acid in the residual bottoms were varied within the ranges specified in the present invention. The results are shown in Table 1 together with those of Example 1 and Comparative Examples 1 to 5. Comparative Example 6 was carried out in the same way as in Comparative Example 1 except that the concentrated residual bottoms contained 6 % by weight of acetic acid. Comparative Example 7 was carried out in the same way as in Comparative Example 1 except that the residual bottoms were cooled and solidified, pulverized, and extracted with hot water for 20 minutes, followed by cooling to room temperature to obtain a catalyst-containing aqueous solution. Comparative Example 8 was carried out in the same way as in Comparative Example 1 except that the residual bottoms were distilled to a benzoic acid content of 13 % by weight.

the resulting catalyst-containing aqueous solution to the above zone; the improvement comprising 1. concentrating said mother liquor until the amount of acetic acid in said bottoms becomes not more than 5 % by weight based on the weight of the residual bottoms and the amount of benzoic acid in said bottoms becomes not less than 15 % by weight based on the weight of the residual bottoms,
2. contacting said bottoms in the hot and molten state with 2 to 5 times their weight of water, and rapidly cooling to a temperature of not more than 50°C., and
3. separating the aqueous solution containing the catalyst from the resulting mixture of granular solid of organic by-products and said catalyst-containing aqueous solution, and recycling the aqueous solution so separated to the catalytic liquid-phase oxidation zone.

2. The process of claim 1 wherein the temperature of the hot and molten bottoms is higher than the melting point of the benzoic acid.

3. The process of claim 1 wherein said concentration is performed until the amount of acetic acid in said bottoms becomes not more than 1 % by weight based Table 1

| Examples (Exp.) and Comparative Examples (Comp.) | Residual bottoms | | | Extracting conditions | | Rate of extracting the catalyst (wt.%) | | | Rate of removal of the solidified organic by-products (wt.%) | Remarks |
|---|---|---|---|---|---|---|---|---|---|---|
| | Acetic acid content (wt.%) | Benzoic acid content (wt.%) | State of bottoms | Amount of water(weight times) | Temperature (°C.) | Co | Mn | Br | | |
| Exp. 2 | 2 | 31.5 | molten | 3 | 40 | 90.8 | 90.6 | 81.2 | 95 | |
| Exp. 1 | 0.5 | 32 | molten | 3 | 40 | 90.6 | 91.8 | 80.6 | 98 | |
| Exp. 3 | 4 | 30.9 | molten | 3 | 40 | 91.0 | 90.8 | 80.4 | 97 | |
| Exp. 4 | less than 0.1 | 16 | molten | 3 | 40 | 90.4 | 91.0 | 80.2 | 98 | cannot be operated for a long time ditto |
| Comp.1 | 10 | 29 | molten | 3 | 40 | 90.8 | 90.9 | 81.3 | 74 | |
| Comp.2 | 0.5 | 32 | molten | 3 | 60 | 91.5 | 92.1 | 84.5 | 77 | |
| Comp.3 | 0.5 | 32 | molten | 1 | 40 | 62.3 | 60.0 | 53.0 | 98 | |
| Comp.4 | 0.5 | 32 | molten | 6 | 40 | 88.0 | 88.5 | 79.0 | 83 | |
| Comp.5 | 0.5 | 32 | molten | 10 | 40 | 91.4 | 90.5 | 81.2 | 69 | |
| Comp.6 | 6 | 30.2 | molten | 3 | 40 | 90.4 | 90.4 | 81.4 | 86 | |
| Comp.7 | 0.5 | 32 | solidified pulverized product | 3 | 100 | 95.5 | 94.0 | 87.5 | * | *inseparable |
| Comp.8 | less than 0.1 | 13 | molten | 3 | 40 | 50.6 | 50.0 | 41.0 | 97 | |

What we claim is:

1. In a process for continuously preparing terephthalic acid by oxidizing para-xylene with molecular oxygen in the liquid phase in acetic acid in the presence of a heavy metal oxidation catalyst, separating and collecting terephthalate acid from the resulting oxidation reaction mixture, recycling a part of the mother liquor to the catalytic liquid-phase oxidation zone either as such or after concentration, concentrating the remainder of the mother liquor, extracting the residual bottoms containing the heavy metal oxidation catalyst and the organic by-products with water, and recycling on the weight of the residual bottoms and the amount of benzoic acid in said bottoms becomes not less than 20 % by weight based on the weight of the residual bottoms.

4. The process of claim 1 wherein the mixture of bottoms and water of step (2) is rapidly cooled to 20° to 50°C.

5. The process of claim 1 wherein said heavy metal oxidation catalyst is a compound of a metal selected from the group consisting of cobalt and manganese.

* * * * *